United States Patent
Miller et al.

(10) Patent No.: US 6,703,246 B1
(45) Date of Patent: Mar. 9, 2004

(54) THERMAL METHOD AND APPARATUS

(75) Inventors: Theodore E. Miller, Midland, MI (US); Charles A. Nielsen, Midland, MI (US); Ray W. Chrisman, Midland, MI (US); Robert E. LaPointe, Midland, MI (US)

(73) Assignee: The Dow Chemical Company, Midland, MI (US)

( * ) Notice: Subject to any disclaimer, the term of this patent is extended or adjusted under 35 U.S.C. 154(b) by 257 days.

(21) Appl. No.: 10/018,668

(22) PCT Filed: Jul. 6, 2000

(86) PCT No.: PCT/US00/18482

§ 371 (c)(1),
(2), (4) Date: Dec. 12, 2001

(87) PCT Pub. No.: WO01/02843

PCT Pub. Date: Jan. 11, 2001

Related U.S. Application Data

(60) Provisional application No. 60/142,486, filed on Jul. 6, 1999.

(51) Int. Cl.$^7$ .......................... G01N 25/20; G01N 7/00
(52) U.S. Cl. ...................... 436/147; 436/149; 436/150; 374/31; 374/41
(58) Field of Search ................ 436/147, 149, 436/150; 374/31, 41

(56) References Cited

U.S. PATENT DOCUMENTS

| | | | | |
|---|---|---|---|---|
| 3,505,024 A | * | 4/1970 | Ishumaru et al. | 422/51 |
| 3,552,207 A | * | 1/1971 | Monk et al. | 374/31 |
| 4,021,307 A | * | 5/1977 | Mosbach | 435/12 |
| 5,249,929 A | | 10/1993 | Miller, Jr. et al. | 417/207 |

FOREIGN PATENT DOCUMENTS

| | | | | |
|---|---|---|---|---|
| DE | 19707044 C1 | * | 8/1998 | G01K/17/00 |
| DE | 19731157 A1 | * | 2/1999 | G01N/25/20 |
| SU | 1113686 A | * | 9/1984 | G01K/17/08 |

OTHER PUBLICATIONS

Brown et al. "Heats of adsorption of ammonia on a zeolite catalyst and an acid–activated clay catalyst determined by flow adsorption microcalorimetry", Langmuir, 2000, v. 16, pp. 4207–4212.*

(List continued on next page.)

*Primary Examiner*—Jill Warden
*Assistant Examiner*—Yelena G. Gakh

(57) ABSTRACT

A thermal method for studying chemical responses, such as catalyzed polymerization reactions that includes the following three steps. The first step is to flow a chemical substance through a conduit, the conduit being in thermal communication with an electrical conductor, the electrical conductor being co-linear with the conduit, the electrical resistance of the electrical conductor being a function of the temperature of the electrical conductor. A length of stainless steel tubing can be used as both the conduit and the conductor. The second step is to flow electricity through the electrical conductor during the first step. The third step is to measure the electrical resistance of the electrical conductor during the second step to determine any change in the temperature of the conduit caused by a response of the chemical substance. An apparatus for studying chemical reactions that includes: a first conduit, the first conduit being an electrical conductor, the first conduit having a first end and a second end, the electrical resistance of the first conduit being a function of the temperature of the first conduit; a source of electricity, the source of electricity in electrical communication with the first conduit so that electricity can be flowed through the first conduit; a volt meter in electrical communication with the first conduit so that the voltage measured by the volt meter is an indication of the temperature of the first conduit.

7 Claims, 2 Drawing Sheets

OTHER PUBLICATIONS

Franz, A.J. et al., "New Operating Regimes and Applications Feasible with Microreactors", Massachusetts Institute of Technology, pp. 33–38 (1997).

Quiram, David J. et al., "Characterization of Microchemical Systems Using Simulations", Massachusetts Institute of Technology, pp. 205–210 (1997).

Zieren, M. et al., "Time–Resolved Calorimetry in a New Type of Micro Fluid Reactor Using Spatically Separated Thin–Film Thermopiles and FIA–Technique", American Institute of Chemical Engineers $2^{nd}$ International Conference on Microreaction Technology, Topical Conference Preprints, pp. 154–163 (1998).

* cited by examiner

THERMAL METHOD AND APPARATUS

This application claims the benefit of provisional application No. 60/142,486 filed Jul. 6, 1999.

BACKGROUND OF THE INVENTION

Thermal methods and apparatus are known for studying chemical responses, such as phase changes or chemical reactions, by flowing a chemical substance through a conduit and measuring a temperature change caused by the response. For example, the conduit can be a covered channel in a plate, the channel being heated to a temperature at which a reaction will occur by a plurality of electrical resistance heaters positioned along the channel while a temperature change caused by a reaction is measured by a plurality of thermopiles which are also positioned along the channel (Zieren et al., American Institute of Chemical Engineers $2^{nd}$ International Conference on Microreaction Technology (1998), Topical Conference Preprints, pages 154–163). Such systems represent an interesting advance in the art but such systems are relatively complex and expensive to manufacture.

SUMMARY OF THE INVENTION

The instant invention provides a solution to the above-mentioned problems. The instant invention is a thermal method for studying chemical responses, comprising the steps of: (a) flowing a chemical substance through a conduit, the conduit being in thermal communication with an electrical conductor, the electrical conductor being co-linear with the conduit, the electrical resistance of the electrical conductor being a function of the temperature of the electrical conductor; (b) flowing electricity through the electrical conductor during step (a); and (c) measuring the electrical resistance of the electrical conductor during step (b) to determine any change in the temperature of the conduit caused by a response of the chemical substance.

The instant invention is also an apparatus for studying chemical reactions, comprising: a first conduit, the first conduit being an electrical conductor, the first conduit having a first end and a second end, the electrical resistance of the first conduit being a function of the temperature of the first conduit; a source of electricity, the source of electricity in electrical communication with the first conduit so that electricity can be flowed through the first conduit; a volt meter in electrical communication with the first conduit so that the voltage measured by the volt meter is an indication of the temperature of the first conduit.

DETAILED DESCRIPTION OF THE INVENTION

Figure 1:
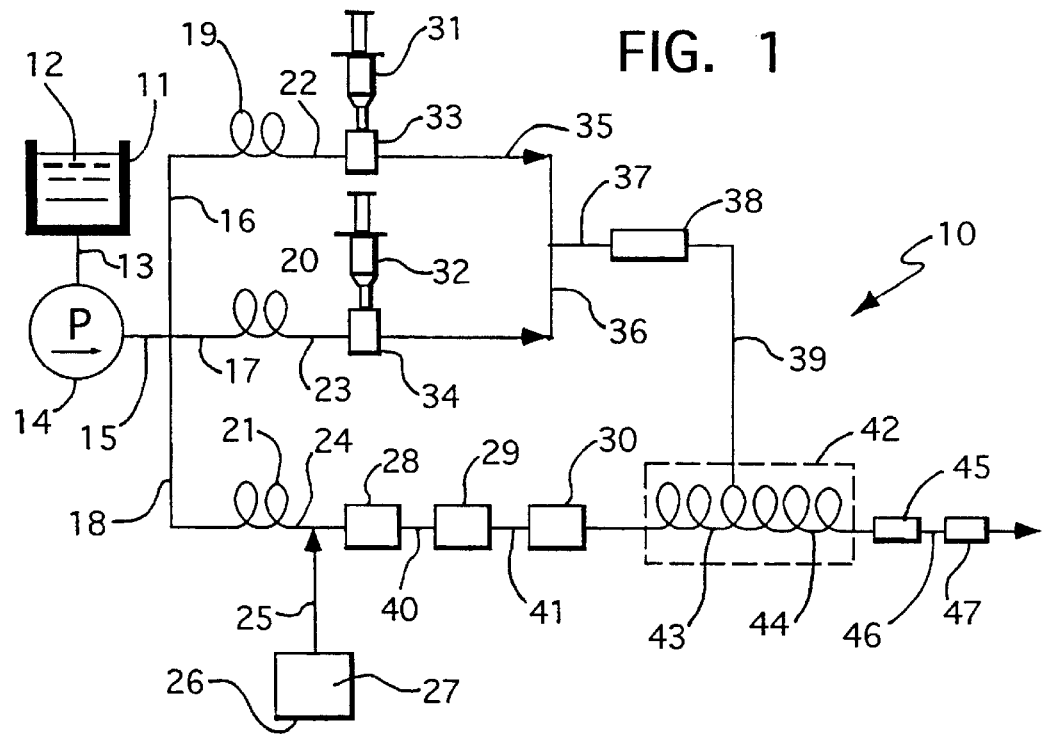
FIG. 1 is a schematic drawing of a specific apparatus embodiment of the instant invention incorporating a coiled tube assembly and a pressure regulator.

Referring now to FIG. 1, therein is shown a schematic drawing of a specific apparatus embodiment 10 of the instant invention. The apparatus embodiment 10 includes a reservoir 11 filled with petroleum naphtha 12 of a grade suitable for catalytically polymerizing ethylene dissolved in the naphtha to polyethylene. A tube 13 conducts naphtha 12 to a High Performance Liquid Chromatography (HPLC) pump 14 set to pump the naphtha 12 at a rate of two milliliters per minute. The pump 14 pumps naphtha 12 to tubing coils 19, 20 and 21 by way of tubing 15, 16, 17 and 18.

A 0.5 micrometer HPLC in-line filter, not shown, is positioned in the tubing 15 to filter the naphtha from the pump 14. The tubing coils 19 and 20 are each 52 feet (16 meters) long, 1/16 inch (1.59 millimeter) outside diameter, 0.004 inch (0.10 millimeter) inside diameter stainless steel tubing. The tubing coil 21 is 10 feet (3 meters) long, 1/16 inch (1.59 millimeter) outside diameter, 0.010 inch (0.254 millimeter) inside diameter stainless steel tubing. Tubing 22 conducts naphtha 12 to HPLC injection valve 33.

The valve 33 has a twenty microliter injection loop, not shown, which is filled using syringe 31. Tubing 23 conducts naphtha 12 to HPLC injection valve 34. The valve 34 has a twenty microliter injection loop, not shown, which is filled using syringe 32. The valves 33 and 34 are automatically actuated using a general-purpose digital computer, not shown. An HPLC autosampler can be used to supply samples to valves 33 or 34 if desired. Tubing 35, 36 and 37 conducts naphtha to a length of tubing 38 that is not an electrical conductor (such as HPLC grade PEEK tubing). Tubing 24 conducts naphtha 12 to in-line mixer 28. Differences between the inside diameters and lengths of the tubing coils 19, 20 and 21 direct most of the flow of naphtha 12 from the pump 14 through the tubing coil 21.

A source 26 of ethylene gas 27 is introduced at a rate of about twenty five cubic centimeters per minute STP into the naphtha flowing in tubing 24 by way of tubing 25. The source 26 of ethylene gas 27 consists of a cylinder of ethylene connected to a pressure regulator (GO Model PR50-1A11C3K111, San Dimas, Calif., set to regulate at 44.2 atmospheres or 4.6 megapascals) connected to a mass flow controller (Porter Instrument Co. Model 201-APBSVBAA, Hatfield, Pa.) connected to a back pressure regulator (GO Model BP60-1A11IEK111, San Dimas, Calif., set to regulate at 40.8 atmospheres or 4.2 megapascals) connected to a check valve (Nupro Model SS-4C1-1/3). The mass flow controller is housed in a thermal enclosure maintained at sixty degrees Celsius (however, the electronic components of the mass flow controller are positioned outside of the thermal enclosure because they will not operate at sixty degrees Celsius).

The ethylene gas 27 is mixed with and dissolved into the naphtha 12 in an in-line mixer 28 (Alletch Part Numbers 20141 and 20147, Deerfield Ill.) and then conducted by tubing 40 to pressure transducer 29 (Validyne Model P55D 4-V-1-60-S-4-B, Northridge, Calif.). Tubing 41 then conducts the naphtha and ethylene to a length of tubing 30 that is not an electrical conductor (such as HPLC grade PEEK tubing). A tubing coil 43 is connected at one end to the tubing 30 and at the other end to the first end of first conduit 44.

The tubing coil 43 is fifty inches (1.3 meters) long, 1/16 inch (1.59 millimeter) outside diameter, 0.050 inch (1.27 millimeters) inside diameter stainless steel tubing. The first conduit 44 is a coil of stainless steel tubing which is seventy inches long (1.8 meters), 1/16 inch (1.59 millimeter) outside diameter and 0.050 1.27 millimeters) inside diameter. The second end of the first conduit 44 is connected to a length of tubing 47 that is not an electrical conductor (such as HPLC grade tubing made from TEFLON brand FEP polymer) via pressure regulator 45 and tubing 46.

As will be discussed below in greater detail, the tubing coil 43 and the first conduit 44 are enclosed in thermal insulation 42 while tube 39 connects tubing 38 with tubing coil 43 and the first end of the first conduit 44.

Figure 2:
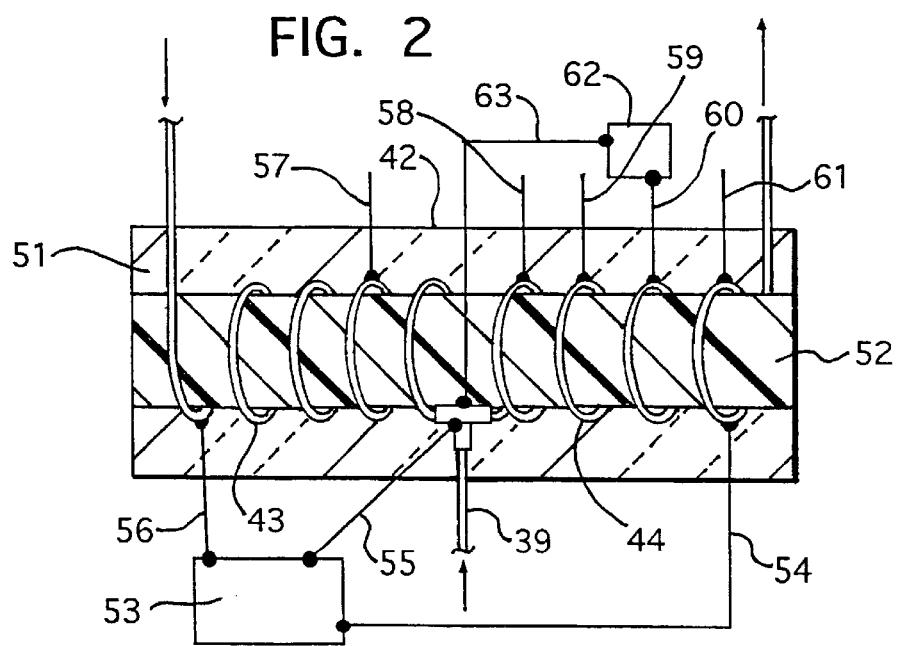
FIG. 2 is a schematic drawing of the coiled tube assembly in greater detail.

Referring now to FIG. 2, therein is shown a schematic drawing of the coiled tube assembly 42, 43, 44 of FIG. 1 in greater detail. The connection of the tube 39, the tubing coil 43 and the first conduit 44 is facilitated by a ¹⁄₁₆ inch (1.59 millimeter) stainless steel tee 50. The tube 39 is a length of ¹⁄₃₂ inch (0.79 millimeters) outside diameter, 0.007 (0.178 millimeters) inside diameter stainless steel tubing which is adapted to the tee 50 by inserting the tube 39 through a three inch (75 millimeter) length, not shown, of ¹⁄₁₆ inch (1.59 millimeter) outside diameter, 0.040 inch (1.02 millimeter) inside diameter stainless steel tubing attached to the tee 50. The tube 39 is inserted in the three inch (75 millimeter) length of stainless steel tubing so that upon insertion the end of the tube 39 bottoms out in the tee 50 and then the tube 39 is withdrawn 0.5 millimeter. The tube 39 is then tightened to the three inch (75 millimeter) length of stainless steel tubing using a ¹⁄₁₆ by ¹⁄₃₂ inch (1.59 by 0.79 millimeter) stainless steel tubing union, not shown.

The tubing coil 43 and first conduit 44 are wound on a cylinder of foamed silicone rubber thermal insulation 52. A cover of foamed silicone rubber thermal insulation 51 is also used so that the tubing coil 43 and first conduit 44 are essentially surrounded by thermal insulation.

A source of electricity 53 (two Kepco Model ATE 36-15M DC power supply units having their positive terminals in common) is connected from the positive common terminal to tee 50 by wire 55. A negative terminal of the source of electricity 53 is connected near one end of the tubing coil 43 by wire 56. The other negative terminal of the source of electricity 53 is connected near the second end of the first conduit 44 by wire 54.

A voltmeter 62 (Keithley Model 2000 six and one half digit multimeter, equipped with a twenty channel multiplexer, Cleveland, Ohio) is connected to tee 50 by wire 63. The voltmeter 62 is also shown connected to an intermediate position of the first conduit 44 by wire 60. The multiplexer of the voltmeter 62 alternatively connects the volt meter 62 to wires 57, 58, 59 or 61 as programmed via the general purpose digital computer, not shown. Wires 54–61 are preferably connected to the tubing coil 43 and first conduit 44 by silver soldering. The non-conductive tubing 30, 38 and 47 shown in FIG. 1 provides electrical isolation for the system shown in FIG. 2.

Figure 3:
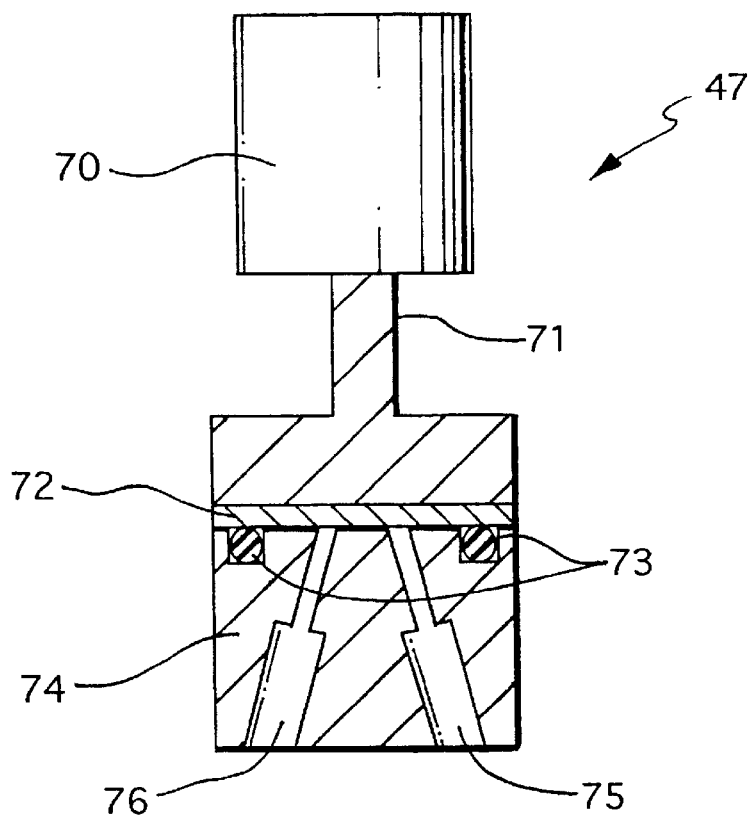
FIG. 3 is a side view, part in full and part in cross-section, of the pressure regulator.

Referring now to FIG. 3, therein is shown a side view, part in full and part in cross-section, of the pressure regulator 45. The pressure regulator 45 comprises a stainless steel body 74 which is drilled through to provide flow passageways 75 and 76. Passageway 75 is connected to tube 46 of FIG. 1. The body 74 is also machined to accommodate an o-ring seal 73. A 127 micrometer thick disk 72 of stainless steel is biased against the body 74 by solenoid 70 (Trombetta Model Q517, having a twenty four volt coil, Monomonee Falls, Wis.) by way of stainless steel ram 71.

The ram 71 in FIG. 3 is shown being broader where it contacts the disk 72 than at the solenoid 70. However, it has recently been found preferable to make the ram 71 a straight cylinder from the solenoid 70 to the disk 72, the such modified ram 71 extending through a washer, the washer being bolted to the body 74 to press the peripheral portion of the disk 72 against the body 74 while the central portion of the disk 72 is free to spring upwards against the modified ram 71.

The amount of current supplied to the solenoid 70 is determined by feedback control using the general-purpose digital computer, not shown, and the signal from the pressure transducer 29. If the pressure transducer 29 senses a higher or lower pressure than desired, then the feedback system feeds less or more current respectively to the solenoid 70 so that the hydraulic pressure in the coil of tubing 43 and the first conduit 44 is controlled to be essentially constant at a pressure of 400 pounds per square inch (2.8 megapascals).

The method of the instant invention can be used to study a chemical response that produces a change in temperature. For example, the instant invention can be used to study a phase change of a chemical, or an exothermic or endothermic chemical reaction involving a chemical substance. The method of the instant invention comprises the following three steps. The first step is to flow a chemical substance through a conduit, the conduit being in thermal communication with an electrical conductor, the electrical conductor being co-linear with the conduit, the electrical resistance of the electrical conductor being a function of the temperature of the electrical conductor.

Referring now to FIG. 2, the first conduit 44 is made of stainless steel tubing. Stainless steel tubing is both a conduit for fluids and an electrical conductor. The electrical resistance of a given length of stainless steel tubing of a given inside and outside diameter is a function of the temperature of the tubing. As a general rule, the electrical resistance of any electrical conductor of a given dimension is a function of the temperature of the conductor.

The first conduit 44 is thus also the electrical conductor of the method of the instant invention and they are obviously in thermal communication. However, it should be understood that other structures can be used. For example, a fused silica capillary tube can be used as the conduit, the fused silica capillary tube being coated (or alternatively lined with) a metal (or other electrical conductor) as the electrical conductor. Or, a channel can be formed in a body as the conduit and a strip of metal can be placed in, on or in thermal communication with the channel as the electrical conductor. The term "thermal communication" means that the temperature change caused by the response of the chemical substance must be thermally conducted to the electrical conductor.

The electrical conductor must be "co-linear" with the conduit. In the system shown in FIG. 2, the conduit and the electrical conductor are the same structure and thus are clearly co-linear. However, electrical conductors placed across and in thermal communication with a channel formed in a body (see, Zieren et al. discussed above) are not co-linear. An electrical conductor of a serpentine, square wave or sine wave placed in thermal communication with a straight length of channel formed in a body are also not "co-linear" with such a channel. Thus, the term "co-linear" means that the electrical conductor and the conduit have essentially parallel longitudinal axes along the conduit and the electrical conductor.

The limitation that the conduit and the electrical conductor be "co-linear" does not mean that the conduit and the electrical conductor must be arranged along a continuous straight line. The conduit and the electrical conductor may be coiled (as shown in FIG. 2) or otherwise configured as long as they are "co-linear" with each other as defined above.

The second step of the instant invention is to flow electricity through the electrical conductor during the first step. Referring now to FIG. 2, the electricity flows in the circuit from the source of electricity 53, through wire 55, through first conduit 44, through wire 54 back to the source of electricity 53. The amount of electrical current flowed through the electrical conductor is generally (but not necessarily) sufficient to significantly increase the temperature of the conduit since the response of the chemical substance is often studied at elevated temperatures. When it is desired to study chemical responses at elevated temperatures, then the system can be preheated by the use, for example, of the coiled stainless steel tubing 43 shown in FIG. 2 which tubing 43 is electrically heated by the source of electricity 53 by way of the wires 56 and 55.

The third step is to measure the electrical resistance of the electrical conductor during the second step to determine any change in the temperature of the conduit caused by a response of the chemical substance. Referring now to FIGS. 1 and 2, if a polymerization catalyst (0.02 Molar in naphtha) is injected by injection valve 33 and a catalyst activator (0.02 Molar in naphtha) is injected at the same time by injection valve 34, then the active catalyst will meet the preheated naphtha and ethylene stream in the tee 50 and flow through the first conduit 44 toward the pressure regulator 45.

Heat is produced when the ethylene polymerizes in the first conduit 44 to produce polyethylene as a reaction product. The heat increases the temperature of the first conduit 44. The electrical resistance of the first conduit 44 can be conveniently measured using the volt meter 62 to measure the voltages of wires 58–61, which voltages are a function of the temperatures of the respective portions of the first conduit 44.

The preheater section (tubing coil 43) is heated by a current of 3.113 amperes. The reactor section (first conduit 44) is heated by a current of 2.389 amperes. The naphtha and ethylene being flowed through the preheater section are heated from ambient temperature to 178 degrees Celsius. The naphtha and ethylene mixture being flowed through the conduit 44 is heated from 178 degrees Celsius to 182 degrees Celsius when no injection of catalyst and catalyst activator is made.

Figure 4:
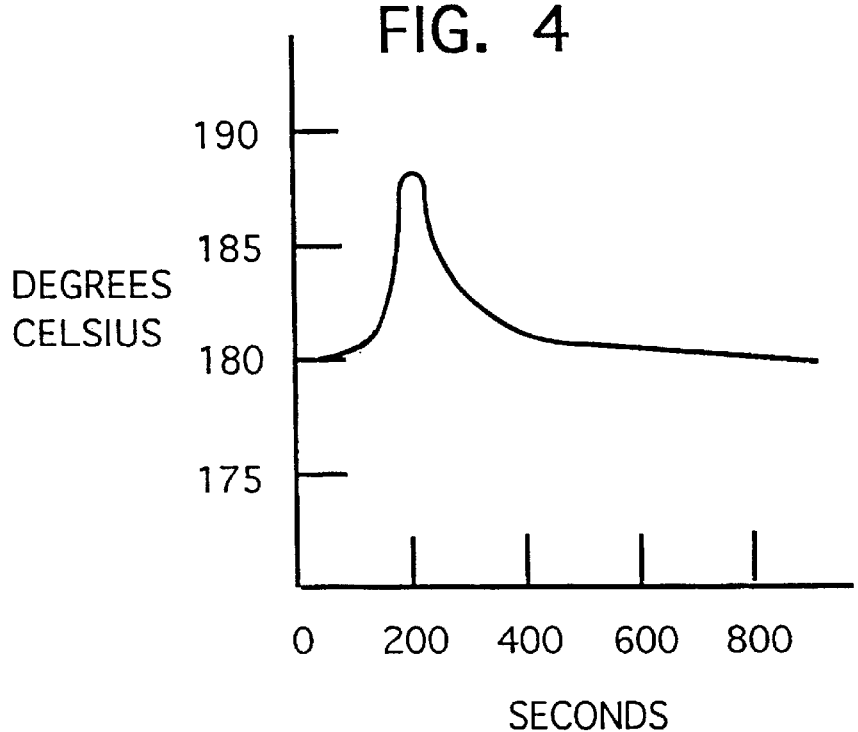
FIG. 4 is a plot of temperature versus time using the instant invention to study a catalyzed polymerization reaction.

Referring now to FIG. 4, therein is shown a plot of temperature of the first conduit 44 between wires 59 and 60 versus time in seconds after the injection of the catalyst and the activator. The plot shown in FIG. 4 indicates that the temperature of the first conduit 44 at first increases from a baseline temperature of 180 degrees Celsius at about 100 seconds, reaches a maximum temperature of about 187 degrees Celsius at about 190 seconds and then decreases to essentially the baseline temperature of 180 degrees Celsius by 800 seconds to produce a temperature "peak".

The temperature peak can be measured by any conventional peak measurement technique such as peak area or peak height. A larger peak is an indication that the catalyst system injected has a greater catalytic effect on the polymerization of the ethylene to polyethylene. The pressure regulator 45 helps to maintain a constant hydraulic pressure in the conduit 44 despite the increase in viscosity in the conduit 44 caused by the polymerization of the ethylene to polyethylene.

The above discussion is made with respect to a specific apparatus and method. Of course the scope of the instant invention is much broader than the above discussed specific apparatus and method. For example, the chemical substance can be continuously flowed into the conduit, the chemical substance can be any reactive chemical or mixture of chemicals such as a mixture of monomers and any fluid can be flowed through the conduit (gas, liquid, supercritical fluid, or a suspension of a material(s) therein).

When the first conduit is a metal tube, then there are a number of factors that need to be considered to optimize the sensitivity of the instant invention. For example, the ratio of the cross-sectional area of the metal of the tube to the cross-sectional area of the channel defined by the tube is preferably less than ten. The system shown in FIG. 1 has such a ratio of about 0.56 because relatively thin wall tubing is used. When 0.02 inch (0.51 millimeter) inside diameter $\frac{1}{16}$ inch (1.59 millimeter) stainless steel tubing is used in the system shown in FIG. 1, then the ratio is about 8.8 and the sensitivity of the system is about ten times lower.

When the first conduit and the electrical conductor are a metal tube, then it is preferable to use a metal such as stainless steel that has a relatively high resistivity. If a metal is used that has a relatively low resistivity, then more current is needed to produce a given power dissipation. Of course, the use of a thinner wall metal tube of any given outside diameter will increase such a voltage drop due to greater electrical resistance per unit of length.

The reaction product flowing from the first conduit can be further analyzed by any number of chemical analysis techniques such as mass spectroscopy, gas chromatography and liquid chromatography. If desired, a plurality of parallel conduit/electrical conductor systems can be used to increase the number of chemical responses that can be studied in any given period of time.

The conduit and electrical conductor are preferably surrounded by thermal insulation. For example, they can even be housed in a vacuum. However, useful results can be obtained without such thermal insulation. For example, useful results can be obtained by moving a stream of air over the conduit and the electrical conductor.

In general, a person of ordinary skill in the art will appreciate the myriad of factors (such as the thermal conductivity, heat capacity and dimensions of the conduit) that will influence any particular application of the instant invention. The primary benefit of the instant invention is that it can provide a less complex and more economical method and apparatus for studying the thermal effects of chemical responses. Another benefit of the instant invention is that it uses a relatively small amount of the chemical(s) being studied.

What is claimed is:

1. A thermal method for studying chemical responses, comprising the steps of:

(a) flowing a chemical substance through a conduit, the conduit being an electrical conductor, the electrical resistance of the electrical conductor being a function of the temperature of the electrical conductor;

(b) flowing electricity through the electrical conductor during step (a); and (c) measuring the electrical resistance of the electrical conductor during step (b) to determine any change in the temperature of the conduit caused by a response of the chemical substance.

2. The method of claim 1, wherein the chemical substance is a chemical reactant, and the response of the chemical substance is a reaction of the chemical reactant to produce a reaction product.

3. The method of claim 2, wherein in step (a) the chemical reactant is dispersed in a liquid flowing through the conduit, wherein in step (b) the conduit is heated by the electricity, and wherein a preselected amount of a catalyst for the reaction is introduced into the liquid so that in step (c) the temperature of the conduit at first increases from a baseline temperature and then decreases to essentially the baseline temperature to produce a measured temperature peak.

4. The method of claim 3, wherein the electrical resistance of the electrical conductor is measured at more than one location of the electrical conductor.

5. The method of claim 3, wherein the hydraulic pressure of the liquid flowing through the conduit is controlled.

6. The method of claim 3, wherein the chemical reactant comprises a monomer and the reaction product comprises a polymer.

7. The method of claim 3, wherein the electrical resistance of the electrical conductor is measured at more than one location of the electrical conductor, wherein the hydraulic pressure of the liquid flowing through the conduit is controlled, wherein the chemical reactant comprises a monomer and wherein the reaction product comprises a polymer.

* * * * *